United States Patent
Malton et al.

(10) Patent No.: US 7,919,452 B2
(45) Date of Patent: Apr. 5, 2011

(54) HYDRO-ALCOHOLIC COSMETIC COMPOSITIONS WITH A DELAYED RELEASE

(75) Inventors: Peter James Malton, Egham (GB); Lynette Anne Makins Holland, Watford (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/880,995

(22) Filed: Sep. 13, 2010

(65) Prior Publication Data

US 2011/0002856 A1    Jan. 6, 2011

Related U.S. Application Data

(63) Continuation of application No. 10/286,076, filed on Nov. 1, 2002, now Pat. No. 7,820,615, which is a continuation of application No. PCT/US01/15166, filed on May 10, 2001.

(51) Int. Cl.
*A61K 8/60* (2006.01)
(52) U.S. Cl. ............... 512/2; 424/47; 424/49; 424/401
(58) Field of Classification Search .................... None
See application file for complete search history.

(56) References Cited

FOREIGN PATENT DOCUMENTS

JP            06287127 A    * 10/1994

\* cited by examiner

*Primary Examiner* — Yelena G Gakh
(74) *Attorney, Agent, or Firm* — Mark A. Charles

(57) ABSTRACT

According to the present invention there is provided a use of a cyclic oligosaccharide for delaying the release of a volatile solvent from a composition, preferably a cosmetic composition, which comprises at least 50% volatile solvent.

There is also provided a use of a cyclic oligosaccharide for reducing the initial harsh solvent odour impact, for example ethanolic/alcoholic odour impact of alcoholic or hydro-alcoholic compositions.

9 Claims, No Drawings

HYDRO-ALCOHOLIC COSMETIC COMPOSITIONS WITH A DELAYED RELEASE

FIELD OF THE INVENTION

The present invention relates to use of cyclic oligosaccharides in a broad range of volatile solvent containing compositions, and in particular in cosmetic compositions, and more particularly in fragrance compositions, comprising at least 50% volatile solvent, to delay the release of volatile solvents from the compositions.

BACKGROUND TO THE INVENTION

It has long been a feature of many types of compositions, including cosmetic compositions and those of other consumer products, that they comprise volatile solvents, often for the purpose, among others, of solubilising ingredients, for example perfume oils, within the composition. The presence of perfume oils within such cosmetic compositions is useful to mask unpleasant odours and to improve consumer acceptance of the composition through delivering a pleasant smell. Indeed, the sole purpose of some cosmetic compositions is the application of a pleasant odour to human or animal skin, hair, or other suitable substrates, by use of these perfume oils. However, for the most part, upon application of such a cosmetic composition containing a volatile solvent, in conjunction with a fragrance, there occurs an initial rapid evaporation of the volatile solvent. This results in a harsh, solvent odour, for example alcoholic odour, which can mask the fragrant impact and reduce consumer acceptance.

Although many attempts have been made to alter the volatility profiles of ingredients within compositions, and particularly within cosmetic compositions, containing volatile solvents, to date, these have mainly focused on altering the volatility profiles of the fragrant materials themselves. For example, it has been suggested that the addition of cyclic oligosaccharides to such cosmetic compositions can alter the volatility profile of the perfume oils giving a longer lasting effect to the fragrance of the cosmetic composition. Previous prior art in this area includes JP-A-50/63126 which discloses the use of perfume and cyclodextrin complexes for use in bath preparations; JP-A-7/241333 which discloses a long-lasting room deodorising composition containing a fragrance and cyclodextrin and U.S. Pat. No. 5,238,915 which discloses pH dependent perfume oil/cyclodextrin complexes within aromatic compositions.

It is now desired to alter the volatility profile of the solvents themselves within cosmetic compositions to, for example, delay the release of the solvent and to reduce the initial harsh solvent odour impact, for example alcoholic/ethanolic. Although some of the prior art cited above discloses compositions that contain cyclic oligosaccharides combined with volatile solvents within a cosmetic composition, they disclose only the durative effects that the addition of the cyclic oligosaccharide has on the release of the fragrance without specifically disclosing any affect that the cyclic oligosaccharide has on the volatility profile of the volatile solvent itself.

Surprisingly, it has now been found that cyclic oligosaccharides can be used within compositions, particularly cosmetic compositions, containing at least 50% volatile solvent to delay the release of volatile solvents and also to reduce the initial harsh ethanolic/alcoholic odour impact of an alcoholic or hydro-alcoholic cosmetic composition.

While not wishing to be bound by theory, it is believed that when cyclic oligosaccharides are added to a cosmetic composition comprising at least 50%, preferably from about 50% to about 99.9%, more preferably from about 60% to about 95%, even more preferably from about 65% to about 75%, by weight, of volatile solvent, the volatile solvent itself competes with the perfume oils for complexation in the cyclic oligosaccharide cavity. This results in some "in situ complexation" between the volatile solvent and the cyclic oligosaccharide. It is believed that the stability profile of this cyclic oligosaccharide:volatile solvent complex is such that there is a delay in the release of the volatile solvent from the composition when applied to a substrate. It is further believed that this results in a perceptible reduction in initial solvent release thus satisfying the consumer desire for a reduced initial harsh solvent odour, for example alcoholic odour, upon cosmetic composition application.

SUMMARY OF THE INVENTION

According to a first aspect of the present invention there is provided a use of a cyclic oligosaccharide within a composition, more preferably a cosmetic composition, comprising at least 50% volatile solvent to delay the release of a volatile solvent.

According to a second aspect of the present invention there is provided a use of cyclic oligosaccharides within a composition, more preferably a cosmetic composition, comprising at least 50% volatile solvent to reduce the initial ethanolic/alcoholic odour impact of an alcoholic or hydro-alcoholic cosmetic composition.

All percentages herein are by weight of the composition unless otherwise indicated. All ratios are weight ratios unless otherwise indicated. Unless otherwise indicated, all percentages, ratios and levels of ingredients referred to herein are based on the actual amount of the ingredient, and do not include solvents, fillers or other materials which may be combined with the ingredient in commercially available products.

All documents referred to herein, including all patents, all patent applications and all articles, are hereby incorporated herein by reference in their entirety unless otherwise indicated.

DETAILED DESCRIPTION OF THE INVENTION

The present invention relates to the use of cyclic oligosaccharides within compositions, particularly cosmetic compositions, comprising a volatile solvent for delaying the release of the volatile solvent.

As used herein the term "to delay the release of a volatile solvent" means to slow down or inhibit the evaporation rate of said volatile solvent from such a composition.

As used herein the term "to reduce the initial harsh ethanolic/alcoholic odour impact of an alcoholic or hydro-alcoholic cosmetic composition" means that, when the fragrance of said composition is assessed, for example by a panel, less ethanolic or alcoholic odours can be detected.

The elements of these compositions are described in more detail below

Cyclic Oligosaccharides

An essential component of the compositions used for the present invention is that they comprise a cyclic oligosaccharide, or mixtures of different cyclic oligosaccharides. As used herein, the term "cyclic oligosaccharide" means a cyclic structure comprising six or more saccharide units. Preferred for use herein are cyclic oligosaccharides having six, seven or eight saccharide units and mixtures thereof, more preferably six or seven saccharide units and even more preferably seven saccharide units. It is common in the art to abbreviate six, seven and eight membered cyclic oligosaccharides to α, β and γ respectively.

The cyclic oligosaccharide of the compositions used for the present invention may comprise any suitable saccharide or mixtures of saccharides. Examples of suitable saccharides include, but are not limited to, glucose, fructose, mannose, galactose, maltose and mixtures thereof. However, preferred for use herein are cyclic oligosaccharides of glucose. The preferred cyclic oligosaccharides for use herein are α-cyclodextrins or β-cyclodextrins, or mixtures thereof, and the most preferred cyclic oligosaccharides for use herein are β-cyclodextrins.

The cyclic oligosaccharide, or mixture of cyclic oligosaccharides, for use herein may be substituted by any suitable substituent or mixture of substituents. Herein the use of the term "mixture of substituents" means that two or more different suitable substituents can be substituted onto one cyclic oligosaccharide. Suitable substituents include, but are not limited to, alkyl groups, hydroxyalkyl groups, dihydroxyalkyl groups, carboxyalkyl groups, aryl groups, maltosyl groups, allyl groups, benzyl groups, alkanoyl groups and mixtures thereof. These substituents may be saturated or unsaturated, straight or branched chain. Preferred substituents include saturated and straight chain alkyl groups, hydroxyalkyl groups and mixtures thereof. Preferred alkyl and hydroxyalkyl substituents are selected from $C_1$-$C_8$ alkyl or hydroxyalkyl groups or mixtures thereof, more preferred alkyl and hydroxyalkyl substituents are selected from $C_1$-$C_6$ alkyl or hydroxyalkyl groups or mixtures thereof, even more preferred alkyl and hydroxyalkyl substituents are selected from $C_1$-$C_4$ alkyl or hydroxyalkyl groups and mixtures thereof. Especially preferred alkyl and hydroxyalkyl substituents are propyl, ethyl and methyl, more especially hydroxypropyl and methyl and even more preferably methyl.

The cyclic oligosaccharides of the compositions used for the present invention are preferably substituted only by either saturated straight chain alkyl or hydroxyalkyl substituents. Therefore, preferred examples of cyclic oligosaccharides for use herein are methyl-α-cyclodextrins, methyl-β-cyclodextrins, hydroxypropyl-α-cyclodextrin and hydroxypropyl-β-cyclodextrins. Most preferred examples of cyclic oligosaccharides for use herein are methyl-α-cyclodextrins and methyl-β-cyclodextrins. These are available from Wacker-Chemie GmbH Hanns-Seidel-Platz 4, Munchen, DE under the tradename Alpha W6 M and Beta W7 M respectively.

Methods of modifying cyclic oligosaccharides are well known in the art. For example, see "Methods of Selective Modifications of Cyclodextrins" Chemical Reviews (1998) Vol. 98, No. 5, pp 1977-1996, Khan et al and U.S. Pat. No. 5,710,268.

In addition to preferred substituents themselves, it is also preferred that the cyclic oligosaccharides of the compositions used for the present invention have an average degree of substitution of at least 1.6, wherein the term "degree of substitution" means the average number of substituents per saccharide unit. Preferred cyclic oligosaccharides for use herein have an average degree of substitution of less than about 2.8. More preferably the cyclic oligosaccharides for use herein have an average degree of substitution of from about 1.7 to about 2.0. The average number of substituents can be determined using common Nuclear Magnetic Resonance techniques known in the art.

The cyclic oligosaccharides of the compositions used for the present invention are preferably soluble in both water and ethanol. As used herein "soluble" means at least about 0.1 g of solute dissolves in 100 ml of solvent, at 25° C. and 1 atm of pressure. Preferably the cyclic oligosaccharides for use herein have a solubility of at least about 1 g/100 ml, at 25° C. and 1 atm of pressure.

The compositions of the present invention preferably comprise from about 0.001% to about 40%, more preferably from about 0.1% to about 25%, even more preferably from about 1% to about 20%, especially from about 1% to about 10%, by weight, and most especially from about 2% to about 6%, by weight, of cyclic oligosaccharide. However, a person skilled in the art will recognise that the levels of cyclic oligosaccharides used in the present invention will also be dependent on the components of the composition and their levels, for example the solvents used or the exact fragrance oils, or combination of fragrance oils, present in the composition. Therefore, although the above limits are preferred, they are not exhaustive.

Volatile Solvent

A second essential element of the compositions for use in the present invention is a volatile solvent, or mixture of volatile solvents, comprising from about 50% to about 99.9%, more preferably from about 60% to about 95%, even more preferably from about 65% to about 75%, by weight, of the final composition. Any volatile solvent suitable for use in the compositions can be used herein. The solvents for use herein are preferably organic volatile solvents.

As used herein, "volatile" refers to substances with a significant amount of vapour pressure under ambient conditions, as is understood by those in the art. The volatile solvents for use herein will preferably have a vapour pressure of about 2 kPa or more, more preferably about 6 kPa or more at 25° C. The volatile solvents for use herein will preferably have a boiling point under 1 atm, of less than about 150° C., more preferably less than about 100° C., even more preferably less than about 90° C., even more preferably still less than about 80° C.

Preferably the volatile solvents for use herein will be safe for use on a wide range of substrates, more preferably on human or animal skin or hair. Suitable volatile solvents include, but are not limited to, those found in the *CTFA International Cosmetic Ingredient Dictionary and Handbook, 7th edition, volume* 2 P1670-1672, edited by Wenninger and McEwen (The Cosmetic, Toiletry, and Fragrance Association, Inc., Washington, D.C., 1997). Conventionally used volatile solvents include $C_3$-$C_{14}$ saturated and unsaturated, straight or branched chain hydrocarbons such as cyclohexane, hexane, heptane, isooctane, isopentane, pentane, toluene, xylene; halogenated alkanes such as perfluorodecalin; ethers such as dimethyl ether, diethyl ether; straight or branched chain alcohols and diols such as methanol, ethanol, propanol, isopropanol, n-butyl alcohol, t-butyl alcohol, benzyl alcohol, butoxypropanol, butylene glycol, isopentyldiol; aldehydes and ketones such as acetone; volatile silicones such as cyclomethicones for example octamethyl cyclo tetrasiloxane and decamethyl cyclopentane siloxane; volatile siloxanes such as phenyl pentamethyl disiloxane, phenylethylpentamethyl disiloxane, hexamethyl disiloxane, methoxy propylheptamethyl cyclotetrasiloxane, chloropropyl pentamethyl disiloxane, hydroxypropyl pentamethyl disiloxane, octamethyl cyclotetrasiloxane, decamethyl cyclopentasiloxane; propellants, and mixtures thereof. Preferred volatile solvents are $C_1$-$C_4$ alcohols and mixtures thereof. More preferred for use herein are $C_1$-$C_4$ straight chain or branched chain alcohols for example methanol, ethanol, propanol, isopropanol and butanol and mixtures thereof, and most preferred for use herein is ethanol.

Fragrance

An optional feature of compositions for use in the present invention is that they comprise greater than about 0.01%, by weight, fragrance material. As used herein the term "fragrance" is used to indicate any odouriferous material. Any fragrance material suitable for use in cosmetic compositions may be used herein but the fragrance will most often be liquid at ambient temperatures. Preferably, the fragrance materials will be present at level of from about 0.01% to about 40%, preferably from about 0.1% to about 30%, more preferably from about 2.5% to about 25%, even more preferably from about 5% to about 20% and most preferably from about 10% to about 15%, by weight, of total composition.

A wide variety of chemicals are known for fragrance uses, including materials such as aldehydes, ketones and esters. More commonly, naturally occurring plant and animal oils and exudates comprising complex mixtures of various chemical components are known for use as fragrances. The fragrance materials useful herein include pro-fragrances such as acetal pro-fragrances, ketal pro-fragrances, ester pro-fragrances, hydrolyzable inorganic -organic pro-fragrances and mixtures thereof. The fragrance material may be released from the pro-fragrances in a number of ways. For example, the fragrance may be released as a result of simple hydrolysis, or by shift in an equilibrium reaction or by a pH-change, or by enzymatic release. The fragrances herein can be relatively simple in their compositions, comprising a single chemical, or can comprise highly sophisticated complex mixtures of natural and synthetic chemical components, all chosen to provide any desired odour.

Preferably the fragrance materials for use in the present invention will have boiling points (BP) of about 500° C. or lower, more preferably about 400° C. or lower, even more preferably about 350° C. or lower. The BP of many fragrance materials are given in *Perfume and Flavor Chemicals (Aroma Chemicals)*, Steffen Arctander (1969). The ClogP value of the fragrance materials useful herein is preferably greater than about 0.1, more preferably greater than about 0.5, even more preferably greater than about 1.0, even more preferably still greater than about 1.2. As used herein the term "ClogP" means the logarithm to base 10 of the octanol/water partition coefficient. This can be readily calculated from a programme called "CLOGP" which is available from Daylight Chemical Information Systems Inc., Irvine Calif., USA. Octanol/water partition coefficients are described in more detail in U.S. Pat. No. 5,578,563.

Suitable fragrance materials can be found in U.S. Pat. No. 4,145,184, U.S. Pat. No. 4,209,417, U.S. Pat. No. 4,515,705, and U.S. Pat. No. 4,152,272. Examples of fragrances useful herein include, but are not limited to, animal fragrance such as musk oil, civet, castoreum, ambergis, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, oilbanum extract, rose extract and mixtures thereof.

Other examples of suitable fragrance materials include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, ciis-3-hexenyl methyl carbonate, citral, citronnellol ans ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral majantol, mayol, melonal, menthol, p-methylacetophenone, methyl anthranilate, methyl cedrylone, methyl dihydrojasmonate, methyl eugenol, methyl ionone, methyl-β-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohaxanol, γ-undecalactone, undecenal, vanillin, veloutone, verdox and mixtures thereof.

Non-volatile Solvents

While the compositions for use in the present invention preferably comprise a volatile solvent they may also comprise "non-volatile" solvents. Suitable non-volatile solvents include, but are not limited to, benzyl benzoate, diethyl phthalate, isopropyl myristate, propylene glycol, dipropylene glycol and mixtures thereof.

Water

The compositions for use in the present invention may also comprise water. If present, the water will preferably comprise from about 0.1% to about 40%, more preferably from about 1% to about 30%, even more preferably from about 5% to about 20%, by weight, of total composition.

Other Optional Ingredients

The compositions for use herein can contain a variety of other optional components suitable for rendering such compositions more cosmetically, aesthetically, or otherwise, acceptable or to provide them with additional usage benefits. Such conventional optional ingredients are well known to those skilled in the art. These include, but are not limited to, any cosmetically acceptable ingredients such as those found in the *CTFA International Cosmetic Ingredient Dictionary and Handbook, 7th edition*, edited by Wenninger and McEwen (The Cosmetic, Toiletry, and Fragrance Association, Inc., Washington, D.C., 1997). As used herein "cosmetically acceptable" means a material (e.g. compound or composition) which is suitable for use in contact with human or animal skin, hair, or other suitable substrate as defined herein below.

There are a number of other examples of additional ingredients that are suitable for inclusion into the present compositions. These include, but are not limited to, alcohol denaturants such as denatonium benzoate; UV stabilisers such as benzophenone-2; antioxidants such as tocopheryl acetate; preservatives such as phenoxyethanol, benzyl alcohol, methyl paraben, propyl paraben; dyes; pH adjusting agents such as lactic acid, citric acid, sodium citrate, succinic acid, phosphoric acid, sodium hydroxide, sodium carbonate; deodorants and anti-microbials such as farnesol and zinc phenolsulphonate; humectants such as glycerine; oils; skin conditioning agents such as allantoin; cooling agents such as trimethyl isopropyl butanamide and menthol; hair conditioning ingredients such as panthenol, panthetine, pantotheine, panthenyl ethyl ether; surfactants such as sodium laueth sulphate and cocoylisothionate and combinations thereof; silicones; hair-hold polymers such as those described in WO-A-94/08557; salts in general, such as potassium acetate and sodium chloride and mixtures thereof. If present, these additional ingredients will preferably be present at a level of less than 25%, by weight, of total composition. More preferably these additional ingredients will be present at a level of less than 10%, by weight, and even more preferably at a level of less than 5%, by weight, of the total composition.

Product Forms

The compositions for use in the present invention may take any form suitable for use, more preferably for cosmetic use. These include, but are not limited to, vapour sprays, aerosols, emulsions, solid sticks, lotions, liquids, creams, gels, sticks, ointments, pastes, mousses and cosmetics (e.g., solid, semi-solid or liquid make-up, including foundations). Preferably the compositions for use in the present invention take the form of a vapour spray.

The compositions for use in the present invention will preferably comprise a cosmetically acceptable carrier. The phrase "cosmetically acceptable carrier", as used herein, means one or more compatible solid or liquid fillers, diluents, extenders and the like, which are cosmetically acceptable as defined herein above. There term "compatible", as used herein, means that the components of the compositions of this invention are capable of being combined with the primary actives of the present invention, and with each other, in a manner such that there is no interaction which would substantially reduce the efficacy of the composition under ordinary use situations. The type of carrier utilised in the present invention depends of the type of product desired and may comprise, but are not limited to, solutions, aerosols, emulsions (including oil-in-water or water-in-oil), gels, solids and liposomes.

Methods of Use

The present invention preferably relates to the use of a cyclic oligosaccharide for delaying the release of a volatile solvent from a composition, particularly a cosmetic composition, for reducing the initial solvent odour impact, for example the ethanolic/alcoholic odour impact from a alcoholic or hydro-alcoholic cosmetic composition. The cosmetic composition itself is preferably used for providing fragrance to a suitable substrate. As used herein the term "suitable substrate" means any surface to which the present composition may be applied without an unduly adverse effect. Suitable substrates include, but are not limited to, human or animal skin or hair, or fabrics. Preferably the use of the present composition is likely application to skin or hair, especially skin.

Other uses for the present invention may include, but are not limited to, compositions outside of the scope of cosmetic compositions. Examples of such compositions include room fragrances, deodorisers for animals or otherwise, home and fabric care products such as furniture polishes, home improvement products such as paints and other spray products such as inhalers and nasal sprays.

The preferred cosmetic compositions of the present invention may be used in a conventional manner for fragrancing a suitable substrate. An effective amount of the composition, typically from about 1 µl to about 1000 µl, preferably from about 10 µl to about 250 µl more preferably from about 25 µl to about 100 µl is applied to the substrate. The composition may be applied by hand but is preferably applied utilising a vaporiser. Preferably, the composition is then left to dry.

EXAMPLES

The following examples further illustrate the preferred embodiments within the scope of the present invention. These examples are given solely for the purposes of illustration and are not to be construed as imitations of the present invention as many variations of the invention are possible without departing from its spirit or scope. Unless otherwise indicated, all ingredients are expressed on a weight percentage of the active ingredient.

Examples I-III

|  | I (% wt) (comparative) | II (% wt) | III (% wt) |
|---|---|---|---|
| Cyclic Oligosaccharide[1] | 0 | 5 | 10 |
| Ethanol | 100 | 95 | 90 |

[1]Beta W7 M1.8 available from Wacker-Chemie GmbH, Hanns-Seidel-Platz 4, Munchen, DE The cyclic oligosaccharide was dissolved in ethanol at room temperature with stirring.

The samples were analysed at 32° C. using Thermo Gravimetric Analysis which recorded the release rate of the volatile solvent over a period of time. The results show that samples containing a cyclic oligosaccharide have a delayed release profile of the volatile solvent compared to the control sample after 10 minutes.

| Example | % volatile Solvent Remaining after 10 mins | Amount of volatile solvent remaining relative to amount of volatile solvent remaining in Eg I |
|---|---|---|
| I | 7.26 ± 3.35 | 1 |
| II | 14.93 ± 1.34 | 2.1 |
| III | 28.61 ± 1.25 | 3.9 |

Examples IV-V

|  | IV (% wt) | V (% wt) |
|---|---|---|
| Cyclic Oligosaccharide[2] | 5 | 10 |
| Ethanol | 95 | 90 |

[2]Alpha W6 M available from Wacker-Chemie GmbH, Hanns-Seidel-Platz 4, Munchen, DE The cyclic oligosaccharide was dissolved in ethanol at room temperature with stirring and the release rate of the volatile solvent was measured as described for Examples I-III. Again the results show that samples containing a cyclic oligosaccharide have a delayed release profile of the volatile solvent compared to the control sample after 10 minutes.

| Example | % volatile Solvent Remaining after 10 mins | Amount of volatile solvent remaining relative to amount of volatile solvent remaining in Eg I |
|---|---|---|
| I | 7.26 ± 3.35 | 1 |
| IV | 19.56 ± 2.62 | 2.7 |
| V | 21.92 ± 0.82 | 3.0 |

Examples VI-VIII

|  | VI (% wt) | VII (% wt) | VIII (% wt) |
|---|---|---|---|
| Fragrance | 10 | 12.5 | 15 |
| Cyclic Oligosaccharide[2] | 2.5 | 5 | 10 |
| Ethanol | 71.75 | 69.5 | 63.5 |
| Deionised Water | 15.75 | 13 | 11.5 |

[2]Beta W7 M1.8 available from Wacker-Chemie GmbH, Hanns-Seidel-Platz 4, Munchen, DE The cyclic oligosaccharide was dissolved in ethanol at room temperature with stirring. Then the fragrance and water were added with stirring.

Examples IX-XI

|  | IX (% wt) | X (% wt) | XI (% wt) |
|---|---|---|---|
| Fragrance | 3 | 2.5 | 3 |
| Cyclic Oligosaccharide[2] | 2 | 5 | 6 |
| Zinc phenolsulphonate | 2 | 1 | 2 |
| Dipropylene Glycol | 30.5 | 14.5 | 17 |
| Isopropyl myristate | 1.5 | 7 | 7 |
| Ethanol | 61 | 70 | 65 |

[2]Beta W7 M1.8 available from Wacker-Chemie GmbH, Hanns-Seidel-Platz 4, Munchen, DE The zinc phenolsulphonate is stirred into the ethanol until fully dissolved. Then the dipropylene glycol is added with stiffing. Next the isopropyl myristate, then the cyclic oligosaccharide and then the fragrance are all added with stiffing. For an aerosol deodorant a propellant such as propane butane (CAP 40®) can be added to Examples IX-XI according to standard industry practice.

When examples II, III, IV-XI were applied to the skin they were found to have found to have a delayed volatile solvent release profile and also to have a reduced initial ethanolic/alcoholic odour impact.

What is claimed is:

1. A composition comprising:
   i) from about 2.5% to about 10%, by weight, of one or more $C_1$-$C_8$ alkyl-substituted cyclic oligosaccharide having an average degree of substitution from 1.6 to about 2.8;
   ii) greater than about 0.01% to about 15%, by weight, of a fragrance;
   iii) a volatile solvent;
   iv) water; and
   v) an aerosol propellant.

2. The composition of claim 1, wherein each of the one or more $C_1$-$C_8$ alkyl-substituted cyclic oligosaccharide is selected from the group consisting of methyl-α-cyclodextrins, methyl-β-cyclodextrins, and mixtures thereof.

3. The composition of claim 1, wherein the one or more $C_1$-$C_8$ alkyl-substituted cyclic oligosaccharide consists of a mixture of methyl-α-cyclodextrins and methyl-β-cyclodextrins.

4. The composition of claim 1, wherein the one or more $C_1$-$C_8$ alkyl-substituted cyclic oligosaccharide consists of methyl-α-cyclodextrins.

5. The composition of claim 1, wherein the one or more $C_1$-$C_8$ alkyl-substituted cyclic oligosaccharide consists of methyl-β-cyclodextrins.

6. The composition of claim 1, wherein the one or more $C_1$-$C_8$ alkyl-substituted cyclic oligosaccharide has an average degree of substitution from about 1.7 to about 2.0.

7. The composition of claim 1, wherein the one or more $C_1$-$C_8$ alkyl-substituted cyclic oligosaccharide has an average degree of substitution of 1.8.

8. The composition of claim 1 wherein said volatile solvent is selected from $C_1$-$C_4$ alkyl alcohols and mixtures thereof.

9. The composition of claim 1 wherein said volatile solvent comprises ethanol.

* * * * *